United States Patent
Kanagaratnam et al.

(10) Patent No.: US 12,279,877 B2
(45) Date of Patent: *Apr. 22, 2025

(54) SYSTEMS AND METHODS FOR TREATING CARDIAC ARRHYTHMIA

(71) Applicant: IMPERIAL COLLEGE OF SCIENCE, TECHNOLOGY AND MEDICINE, London (GB)

(72) Inventors: Prapa Kanagaratnam, London (GB); Nick Linton, London (GB); Darrel Francis, London (GB)

(73) Assignee: Imperial College Innovations Limited, London (GB)

( * ) Notice: Subject to any disclaimer, the term of this patent is extended or adjusted under 35 U.S.C. 154(b) by 388 days.

This patent is subject to a terminal disclaimer.

(21) Appl. No.: 17/745,342

(22) Filed: May 16, 2022

(65) Prior Publication Data

US 2023/0019503 A1   Jan. 19, 2023

Related U.S. Application Data

(63) Continuation-in-part of application No. 16/606,514, filed as application No. PCT/GB2018/051078 on Apr. 25, 2018, now Pat. No. 11,331,033.

(30) Foreign Application Priority Data

Apr. 25, 2017   (GB) .................................... 1706561

(51) Int. Cl.
*A61B 5/00*   (2006.01)
*A61B 5/287*   (2021.01)
*A61B 5/367*   (2021.01)

(52) U.S. Cl.
CPC .............. *A61B 5/367* (2021.01); *A61B 5/287* (2021.01); *A61B 5/7203* (2013.01); *A61B 2576/023* (2013.01)

(58) Field of Classification Search
CPC ....... A61B 5/367; A61B 5/287; A61B 5/7203; A61B 2576/023
See application file for complete search history.

(56) References Cited

FOREIGN PATENT DOCUMENTS

| | | |
|---|---|---|
| WO | 2014174274 A1 | 10/2014 |
| WO | 2014182842 A1 | 11/2014 |
| WO | 2018197865 A1 | 11/2018 |
| WO | 2019118436 A1 | 6/2019 |

OTHER PUBLICATIONS

International Search Report and Written Opinion of International Application No. PCT/GB2023/051270 dated Sep. 13, 2023, 19 pages.

(Continued)

*Primary Examiner* — Scott M. Getzow
(74) *Attorney, Agent, or Firm* — Wegman Hessler Valorie

(57) ABSTRACT

Apparatus for monitoring activation in a heart comprises a probe 101, a plurality of electrodes 102 supported on the probe and extending over a detection area of the probe, the detection area being arranged to contact a detection region of the heart. Each of the electrodes 102 is arranged to detect electrical potential at a respective position in the heart during movement of a series of activation wave fronts across the detection region. A processor is arranged to analyse the detected electrical potentials to identify a propagation direction of at least one of the wave fronts, and to generate an output indicative of that direction.

17 Claims, 10 Drawing Sheets

(56) References Cited

OTHER PUBLICATIONS

Dosdall D J et al: "Differential Electrograms Computed From Unipolar Endocardial recordings Improve Purkinje Activation Identification", Computers in Cardiology, 2009, IEEE, Sep. 13, 2009, 4 pages.
Magnus Holm et al: "A New Method for Analysis of Atrial Activation During Chronic Atrial Fibrillation in Man", Transactions on Biomedical Engineering, IEEE, USA, vol. 43, No. 2, Feb. 1, 1996, 13 pages.
Unger Laura et al: "Noise Quantification and Noise Reduction for Unipolar and Bipolar Electrograms", 2019 Computing in Cardiology (CINC), Creative Commons, Sep. 8, 2019, 4 pages.
Du Dongping et al: "Detection of the Propagating Direction of Electrical Wavefront in Atrial Fibrillation", 2016 38th Annual International Conference of the IEEE Engineering in Medicine and Biology Society (EMBC), IEEE, Aug. 16, 2016, 4 pages.

SYSTEMS AND METHODS FOR TREATING CARDIAC ARRHYTHMIA

CROSS REFERENCE TO RELATED APPLICATIONS

The present application is a continuation-in-part application of U.S. patent application Ser. No. 16/606,514 filed Oct. 18, 2019, and claims the priority benefit of PCT Application PCT/GB2018/051078 filed Apr. 25, 2018, and Great Britain Patent Application Serial No. 1706561.6 filed Apr. 25, 2017, all of which are incorporated by reference herein.

FIELD OF THE INVENTION

The present invention relates to the detection and pictorial representation of cardiac activation, and in particular of the progression of activation through the heart. It has application in locating sites suitable for ablation therapy, for example to cure atrial fibrillation.

BACKGROUND TO THE INVENTION

Irregular heart beat (arrhythmia) is commonly treated with ablation therapy in a cardiac catheter laboratory. A method is needed to identify where the ablation therapy should be delivered, in order to cure the arrhythmia without having to ablate an unnecessarily large amount of the heart.

Parts of the heart become electrically activated in sequence. In health, this is an orderly and normal sequence, proceeding from the sinus node, through regions of the atrium in a stereotyped pattern. In this type of activation each point on the heart has a well defined propagation direction in which the activation progresses as it passes that point. In arrhythmias, the sequence is not normal. The abnormal sequences may be of two categories: those that show a surface ECG pattern that is obviously regular and repetitive, or those that appear to be irregular and do not show a simple repeating pattern.

Fibrillatory electrical activation of the myocardium is one of the most common causes of cardiac morbidity and mortality. It can affect either the atrium (atrial fibrillation) or the ventricle (ventricular fibrillation). Mathematical modelling and in-vitro studies have suggested that fibrillatory electrical activation can often be driven by electrical rotors (Skanes A C, Mandapati R, Berenfeld O, Davidenko J M, Jalife J. Spatiotemporal periodicity during atrial fibrillation in the isolated sheep heart. Circulation 1998; 98:1236-48) and that a small number, for example one to three, of such rotors may be sufficient to maintain fibrillation in the human heart. If the origin of these rotors can be identified and targeted for treatment, then it may be possible to prevent the death and suffering caused by fibrillatory electrical activation.

An alternative explanation for fibrillatory activity is that there exist areas of the heart that act as focal sources of atrial fibrillation giving rise to focal activation. The repetitive firing from these areas may then perpetuate atrial fibrillation (Lee M S, Sahadevan J, Khrestian C M, Durand D M, Waldo A L. High Density Mapping of Atrial Fibrillation During Vagal Nerve Stimulation in the Canine Heart: Restudying the Moe Hypothesis. Journal of Cardiovascular Electrophysiology, 24: 328-335. doi:10.1111/jce.12032).

Atrial activation during human atrial fibrillation is not identical between different patients. It can be anywhere on a spectrum between completely organised to highly disorganised activation (Kanagaratnam P, Cherian A, Stanbridge R D, Glenville B, Severs N J, Peters N S Relationship between connexins and atrial activation during human atrial fibrillation. J Cardiovasc Electrophysiol. 2004 February; 15(2):206-16). The current state of the art is that, using multi-electrode catheters, it is possible to map the activation sequences using isochronal mapping. i.e. mapping of the timing of activation over the cardiac surface with points which activate at the same time being identified, eg by the same colour. However this is time-consuming and needs careful expert assessment of each electrogram and comparing it to neighbouring electrograms in order to identify the local activation time and produce an isochronal map.

Despite the use of isochronal mapping for human atrial fibrillation using epicardial multi-electrodes catheters for many years, there is no method for identifying rotors or focal sources that can be implemented to operate satisfactorily in independent hands. There are several possible explanations for this. First, most techniques have not been able to map the whole chamber with sufficient resolution. Second, it has been assumed that rotors or focal sources will be visible continuously over many seconds or minutes, and remain in the same location. However, rotors and sources may move or have unstable activation.

WO2014/174274 discloses a system for locating and representing activation wave fronts and rotors. The present invention aims to further improve on the systems described therein.

SUMMARY OF THE INVENTION

The present invention provides apparatus for monitoring activation in a heart, the apparatus comprising a probe, a plurality of electrodes supported on the probe and each arranged to detect electrical potential, for example at a respective position in the heart during a series of activations, and processing means arranged to analyse the detected electrical potentials, for example to identify a propagation direction of the activation, and optionally to generate an output indicative of that direction.

The processing means may be arranged to record values of the electrical potential at each of the electrodes as a respective unipolar electrogram.

The processing means may be arranged to perform filtering on the unipolar electrograms to filter out noise from the unipolar electrograms.

The processing means may be arranged, in filtering the unipolar electrograms, to filter out from the unipolar electrograms noise features which are common to a plurality of the unipolar electrograms. The processing means may be arranged to retain in the unipolar electrograms, features which are unique to each of the unipolar electrograms.

The processing means may be arranged, in filtering the unipolar electrograms, to define a multi-electrode model which defines the unipolar signal at each of the electrodes, and to identify a best fit of the model to the unipolar electrograms.

The model may define the difference between each of a plurality of pairs of the unipolar signals and the processing means may be arranged to determine from the unipolar electrograms measured values of said differences. The best fit may be arranged to include said differences.

The processor may be configured to identify at least one of the wavefronts as belonging to one of a plurality of classifications depending on at least one of its shape, its position, and its direction of travel.

The present invention further provides apparatus for monitoring activation in a heart, the apparatus comprising a probe, a plurality of electrodes supported on the probe and extending over a detection area of the probe, the detection area being arranged to contact a detection region of the heart, wherein each of the electrodes is arranged to detect an electrical potential at a respective position in the heart during movement of a series of activation wavefronts across the detection region, a display screen, and a processor configured to: record the detected electrical potential at each of the electrodes as a unipolar electrogram; forming an electrogram combination which is a linear combination of at least two of the unipolar electrograms; and filter out noise in the unipolar electrograms based on the degree to which the noise is more present in the individual unipolar electrograms than it is in the electrogram combination.

The linear combination may be affected more by a change in just one of the two electrical potentials than it is by the same change in both of the two electrical potentials.

The linear combination may be a subtraction of values in one unipolar electrogram from values in another unipolar electrogram. The values in each of the unipolar electrograms may be weighted.

The processor may be configured to filter out the noise by: defining a model of the electrical potentials at all of the electrodes; defining a voltage combination which is a linear combination of at least two of the electrical potentials in the model; finding a best fit of the model and the voltage combination to the unipolar electrograms and the electrogram combination.

The processor may be configured to define a measurement matrix recording the unipolar electrograms and the electrogram combination, and an observer matrix which relates the measurement matrix to the model. The observer matrix may define a plurality of voltage combinations each of which is a linear combination of a different pair of the electrical potentials.

The voltage combination may be a difference between two of the electrical potentials.

The processor may be configured to define a weighting for each of the unipolar electrograms and the electrogram combination or combinations. The weightings may be applied in the finding of the best fit, for example in a least squares fit method. The weightings may be chosen to determine the frequency response. This enables the system to retain the most useful information from all of the measurements. For example it may be used to retain higher frequency information from the electrogram combinations and lower frequency information from the unipolar electrograms.

The processor may be configured to analyse each of the unipolar electrograms, for example using a convolution with an inverse function of time, to identify any tissue activation features that they contain which are indicative of one of the activation wavefronts The electrodes may extend over a detection area of the probe. The detection area may be arranged to contact a detection region of the heart.

The processing means may be arranged to analyse the detected potentials to identify a plurality of propagation directions of a single wavefront as the wavefront moves across the detection region.

The processing means may be arranged to allocate the electrodes to a plurality of groups. The processing means may be arranged, within each group, to allocate the electrodes into a plurality of pairs each comprising a first electrode and a second electrode. The processing means may be arranged, for each of the pairs, to determine the time delay between a wave front passing the first electrode and the wavefront passing the second electrode. The processing means may be arranged, from the time delays, to determine a direction of propagation of the wavefront past the group.

The processing means may be arranged to identify a plurality of wavefronts and a plurality of propagation directions of each of the plurality of wavefronts.

The apparatus may further comprise display means, such as a display screen. The processing means may be arranged to control the display means to generate a display indicative of the direction or directions.

The processing means may be arranged to analyse detected potentials for a plurality of positions of the probe in the heart. The processing means may be arranged to control the display means to indicate simultaneously the direction of propagation at each of the positions of the probe.

The processing means may be arranged, for each wavefront passing the detection region, to define a series of update intervals over the transition period during which the wavefront crosses the detection region. The processing means may be arranged, for each of the update intervals, to determine a propagation direction. The processing means may be arranged to control the display to generate an image comprising a series of features. One of the features may be added after each update interval in a position determined by the propagation direction for that update interval.

The processing means may be arranged to identify an update interval in which a wavefront first enters the detection region and to control the display in response thereto to add one of the features at an origin position of the image, whereby each wavefront crossing the detection region is indicated by a line of said features extending away from the origin position.

The processing means may be arranged to determine the direction of propagation at each of a plurality of points in the detection region. The processing means may be arranged to determine from the directions of propagation a value for the curl, or divergence, of the propagation direction at at least one point in the detection region. The processing means may be arranged, from the at least one value of the curl or divergence, to locate a source of fibrillation within the detection region.

The present invention further provides a method of locating a source of fibrillation of a heart, the method comprising: providing a probe having a detection area, and a plurality of electrodes supported on the probe and extending over the detection area of the probe, placing the detection area of the probe in contact with a detection region of the heart, detecting the electrical potential of each of the electrodes, for example, during movement of a series of activation wavefronts across the detection region, analysing the detected electrical potentials to identify at least one propagation direction of one or more of the wavefronts, and identifying from the propagation directions the location of a source of fibrillation.

The step of analysing the detected potentials may identify a plurality of propagation directions of a single wavefront as the wavefront moves across the detection region.

The step of analysing the detected electrical potentials may comprise allocating the electrodes to a plurality of groups, and within each group allocating the electrodes into a plurality of pairs each comprising a first electrode and a second electrode. It may further comprise for each of the pairs determining the time delay between a wave front passing the first electrode and the wavefront passing the second electrode. It may further comprise, from the time delays, determining a direction of propagation of the wavefront past the group.

The method may comprise identifying a plurality of wavefronts and a plurality of propagation directions of each of the plurality of wavefronts.

The method may further comprise generating an image indicative of the direction or directions.

The method may further comprise analysing detected potentials for a plurality of positions of the probe in the heart, and generating the image so as to indicate simultaneously the direction of propagation at each of the positions of the probe.

The method may further comprise, for each wavefront passing the detection region, defining a series of update intervals over the transition period during which the wavefront crosses the detection region. The method may further comprise, for each of the update intervals determining a propagation direction. The image may comprise a series of features, One of the features may be added after each update interval in a position determined by the propagation direction for that update interval.

The method may further comprise identifying an update interval in which a wavefront first enters the detection region. Generating the image may comprise adding one of the features at an origin position of the image, whereby each wavefront crossing the detection region may be indicated by a line of said features extending away from the origin position.

Identifying at least one propagation direction of each of the wavefronts may comprise determining the direction of propagation at each of a plurality of points in the detection region. Identifying the location of a source of fibrillation may comprise determining from the directions of propagation a value for the curl or divergence of the propagation direction at least one point in the detection region.

The present invention further provides a method of treating cardiac fibrillation comprising locating a source of fibrillation according to the method described above and ablating a region of the heart at the location of the source of fibrillation.

The system may further comprise any one or more features, in any combination, of the embodiments of the invention which will now be described by way of example only with reference to the accompanying drawings.

DETAILED DESCRIPTION

Figure 1:
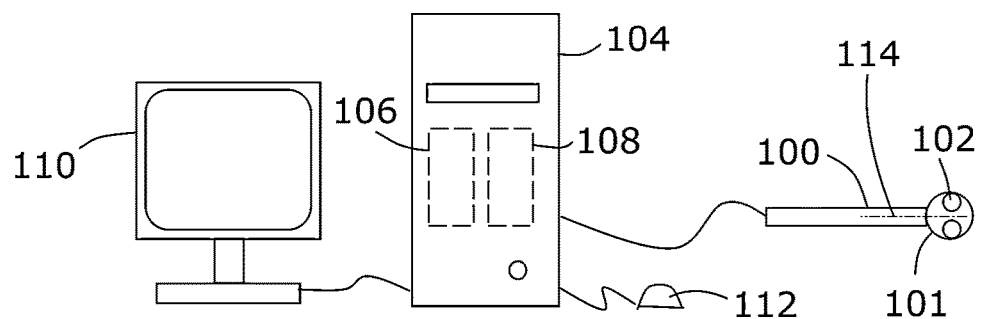
FIG. 1 is a diagram of a system according to an embodiment of the invention.

Referring to FIG. 1, a cardiac monitoring system according to an embodiment of the invention comprises a catheter 100 having a probe 101 at one end with a set of electrodes 102 located on it. Each of the electrodes 102 is connected independently through the probe catheter 100 to a computer 104 which is arranged to acquire, store and analyse the voltages detected by the electrodes 102. Specifically the computer 104 comprises a memory 106 and a processor 108. The processor is arranged to sample the voltages detected by the electrodes 102 at a regular sample rate and store the values of the sampled voltages, which form a time series of sample values, in the memory 106, and then to analyse the stored voltage values so as to analyse the activation of the heart in the area contacted by the probe 101. Specifically the data can be analysed to identify focal targets within areas of irregular activation. The processor 108 is arranged to generate from the sampled voltage data, an image data set which it then provides to the display screen 110 which displays an image showing the activation pattern in the heart so that a user can interpret it. The probe 101 can be moved from region to region within the heart to focus attention in the regions where the targets are suspected.

The catheter 100 may further comprise an ablation tip 114 which is connected to a radio frequency (RF) power source. The ablation tip 114 can therefore be used for ablation of regions of the heart which are found to be sources of atrial fibrillation, whether focal sources or rotors. The catheter may for example be a Smart-Touch catheter (Biosense-Webster) or a Tacticath catheter (Abbott). Alternatively separate catheters may be used, one such as the AFocus catheter for diagnosis or location of the source of fibrillation, and the other for example a Navistar catheter for ablation.

Figure 2:
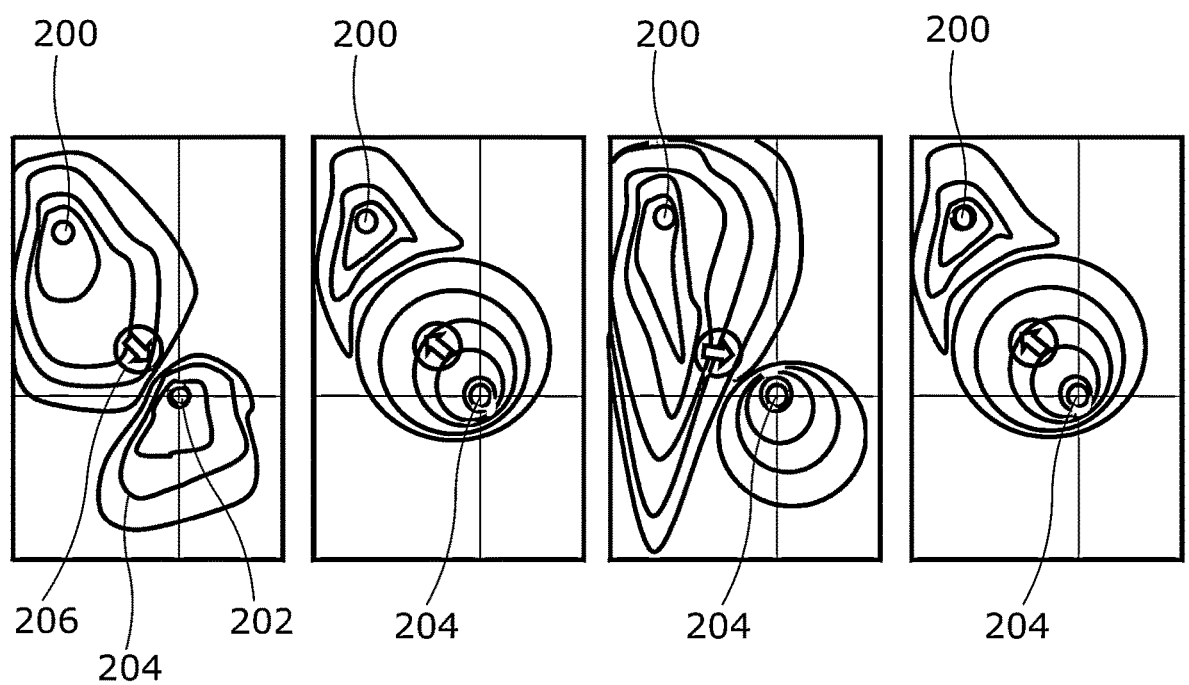
FIG. 2 is a set of plots showing variation in wave front propagation direction during atrial fibrillation.

The variety of directions of activation wave fronts at a particular location is illustrated for example in FIG. 2. In the region shown, there are two focal sources 200, 202 shown both of which act as sources of activation wave fronts 204. Due to the irregularity of, and lack of synchronisation between, the two sources, the activation waves from the two sources interact in a manner which varies considerably over time. Therefore if a point such as that 206 shown in FIG. 2 is considered, the direction in which wave fronts will cross that point will in general be different for each wave front. While some, such as the first, second and fourth shown, may be generally in the direction away from one of the sources, others, such as the third shown, will be in different directions as a result of the interference between waves from the two sources.

The system is therefore arranged to analyse the signals from the probe electrodes 102 so as to detect each of the different directions of propagation across each point, and then to analysis those as will be described in more detail below so as to locate, and enable treatment of, the rotors or other problematic regions.

The data acquisition, data processing, and image display will now be described in more detail. The processor 108 is arranged to perform each of these steps. For any particular position of the catheter 100, a stream of raw signal data is acquired from each of the numerous electrodes 102 of the catheter. The position of each electrode 102 is known through one of a variety of methods well known to those skilled in the art, such as those marketed as CARTO™ or NavX™. The following steps are then carried out by the system under the control of the processor 108. They are described here in sequence but they can occur almost simultaneously so that the operator sees the activation pattern at any position of the catheter 100 after only a minimal delay, for example less than a second.

Firstly the electrical data is acquired. For this step the catheter 100 and computer 104 are arranged to acquire unipolar or bipolar electrogram data. A standard definition of unipolar electrogram data for a particular site is the potential difference between an intracardiac electrode at that site and a reference potential, for example at Wilson's central terminal, or any other combination of skin surface electrodes. Alternatively, a unipolar electrogram can be defined as the potential difference recorded between an intracardiac electrode and an electrode placed within the body at a site outside the heart, for example in the inferior vena cava, a large vein adjacent to the heart in which an electrode can very conveniently be located. Therefore for unipolar electrogram data a further electrode, not shown, is also provided and connected to the computer to provide the reference signal in known manner.

Alternatively bipolar electrogram data can be used, being defined as the potential difference between two of the intracardiac electrodes 102. In this case no further reference electrode is needed.

Whether unipolar or bipolar electrogram signals are used, the electrical signal (voltage) from each electrode (or electrode pair) is sampled at a regular sample frequency and the sampled values stored in memory for analysis.

Figure 3:
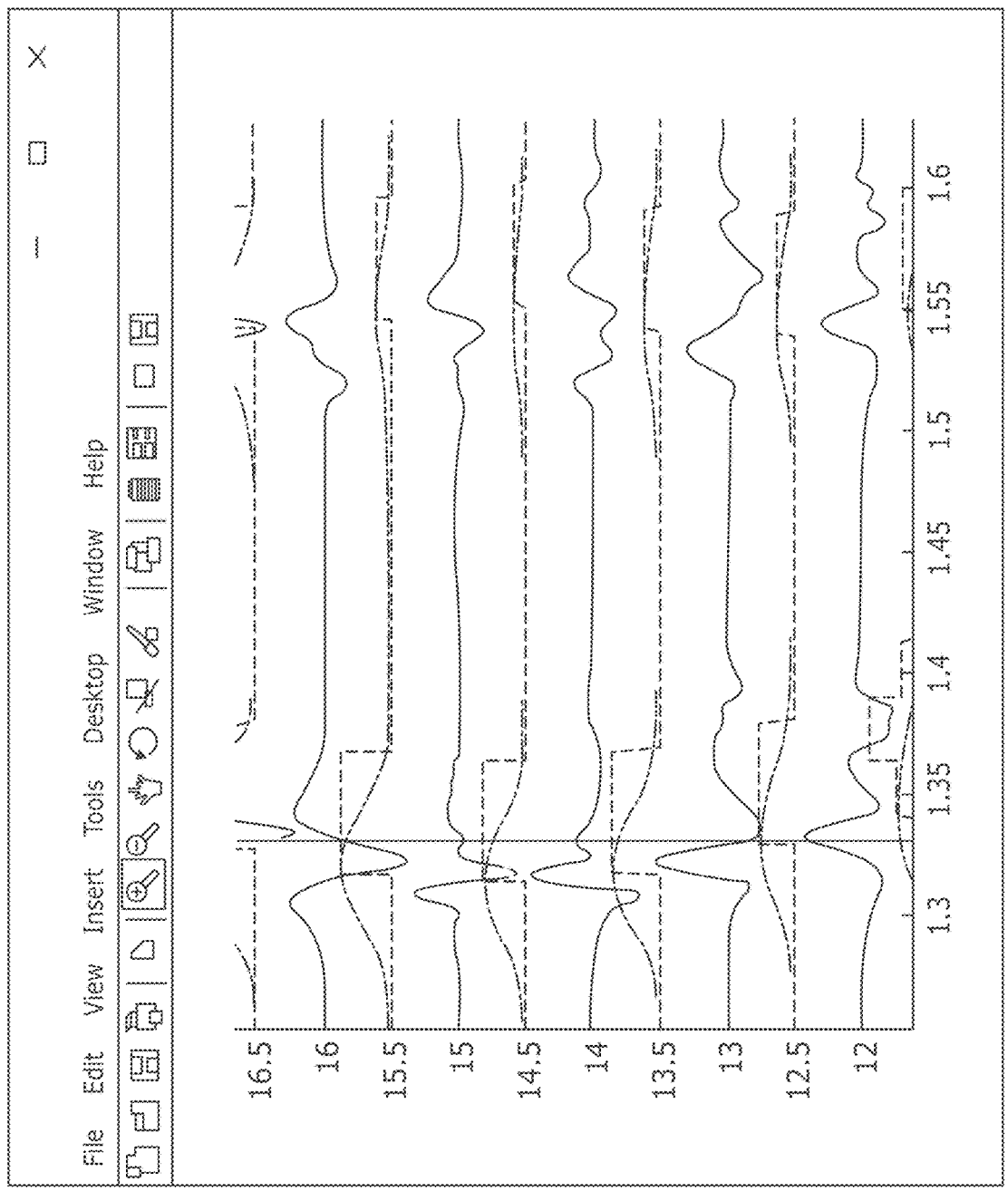
FIG. 3 is a plot of a windowing function used in the system of FIG. 1.

Then, the electrogram data obtained is filtered to remove noise and baseline artefact. A variety of filtering algorithms are well known to those skilled in the art. It is possible to apply one or more in sequence, using software programs coded operating on the microcomputer system 104 as in this embodiment. In other embodiments the processing is performed by hardware circuitry specifically designed or customised for filtering, known as digital signal processing hardware. For example a simple band pass filter may be used, which may be at 10-250 Hz. An example of filtered electrogram signals is shown in FIG. 3, in which the electrogram data for electrodes numbered 12, 13, 14, 15 and 16 are shown, together with the results of analysis of pairs of the electrograms which are shown on lines 12.5, 13.5, 14.5 and 15.5, as will be described in more detail below.

Figure 4:
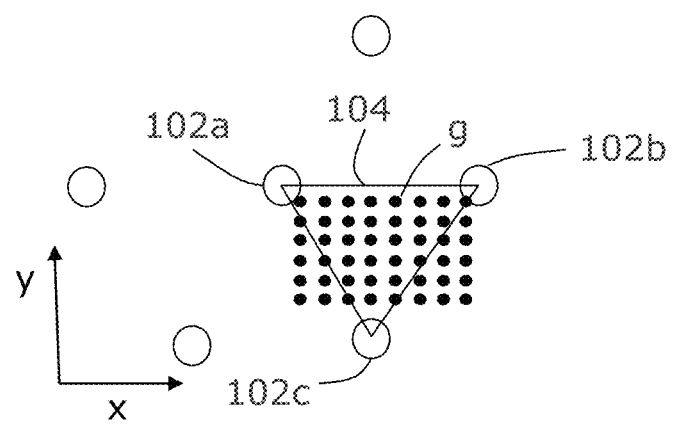
FIG. 4 is a plot illustrating an algorithm for determining relative activation times used in the system of FIG. 1.

Referring to FIG. 4 for the following discussion, the electrode locations at which the electrograms are obtained will be referred to as 'nodes'. The nodes are triangulated, i.e. grouped into sets of three nodes 102a, 102b, 102c which form a triangle. Each edge 104 of the triangle extends between a pair of the three nodes, e.g. 102a and 102b, with a corresponding pair of electrograms. Each of these three pairs of electrograms is then processed to determine a time delay between the activation times of the two electrodes in the pair. From the three time delays, the direction and speed of the wave front passing the group of three nodes can be determined. For example each direction may be calculated and defined as components in two orthogonal directions x, and y, of a vector of unit length in the direction of propagation.

In order to determine each of the time delays an autocorrelation algorithm is used, performed by the processor 108 to compare the activation times of the two electrodes in each electrogram pair. Autocorrelation is used because closely spaced electrograms usually have a morphology that is similar. Autocorrelation provides a way of determining relative times of activation between the pair.

Let represent an electrogram time series with n samples:

$$e=[e_1,e_2,e_3,\ldots,e_N]$$

A windowing function is applied to the time series in order to select information that corresponds to a particular time and avoids multiple activations falling within the same window.

$$w=[w_{-k},w_{-k+1},\ldots,w_{-1},w_0,w_1,\ldots,w_{k-1},w_k]$$

Figure 5:
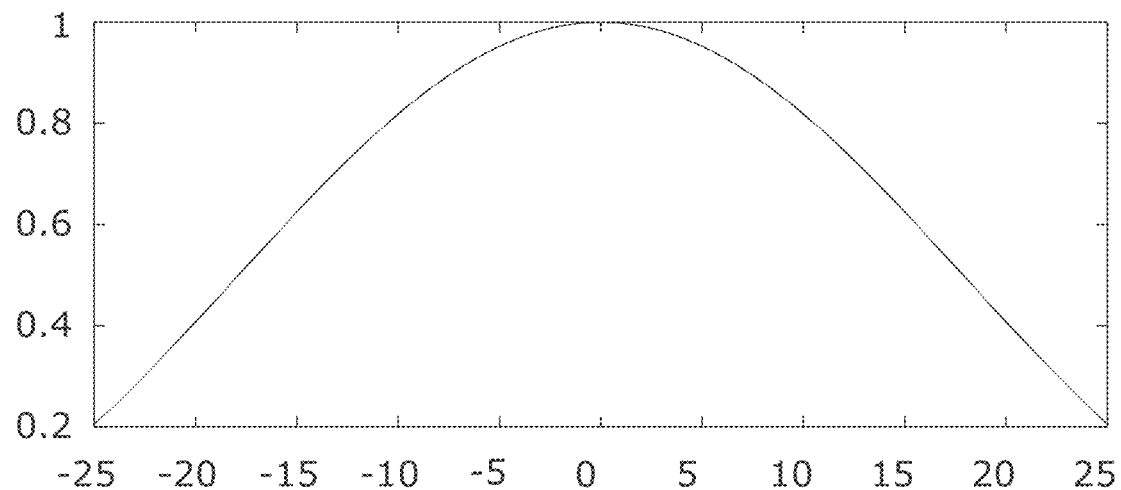
FIG. 5 shows an image displayed in the system of FIG. 1 showing multiple propagation directions.

This is shown in FIG. 4, with k=25. The total width of the windowing function is 51 (2k+1) samples, corresponding to approximately 100 ms at a sample rate of 500 Hz. As can be seen from FIG. 5, the windowing function is centred on one sample, indicated as sample 0 in FIG. 5, and has its highest value for sample 0. It falls away to zero at the samples at either end of the window, i.e. −k and +k.

Next, the windowed electrogram $e_w(t)$ at time t, corresponding to one of the sample times, is obtained by multiplying the electrogram values, centred on the sample at time t, with the values of the windowing function:

$$e_w(t)=[e_{t-k}\cdot w_{-k},e_{t-k+1}\cdot w_{-k+1},\ldots,e_{t-1}\cdot w_{-1},e_t\cdot w_0,e_{t+1}\cdot w_1,\ldots,e_{t+k-1}\cdot w_{k-1},e_{t+k}\cdot w_k]$$

Then windowed electrograms from two neighbouring nodes are selected—$e_{1w}$ and $e_{2w}$.

Next, cross correlation R(t,Δ) between the two windowed electrograms is determined for all sample times t and all possible time delays (i.e. differences in time of activation between the two electrodes in the pair) Δ within a range:

$$R(t,\Delta) = e_{1w}\left(t-\frac{\Delta}{2}\right)\cdot\left(e_{2w}\left(t+\frac{\Delta}{2}\right)\right)^{\tau}$$

For example, for a catheter where electrograms are recorded 10 mm apart, allowing for slow conduction of 0.5 m/s, this corresponds to a maximum transit time of 20 ms. Therefore, values of Δ may be limited to ±20 ms.

Next, to find values for t and Δ local maxima in R(t,Δ) are determined. Only maxima above a sensitivity threshold are considered. At each local maximum, $R(t_{max},\Delta_{max})$, the relative timing of two electrodes $e_1$ and $e_2$ is given by $\Delta_{max}$. Approximate timing $T_{e1}$ and $T_{e2}$ of activation at each of the two electrodes in the pair can be determined as follows:

$$T_{e1} = t_{max} - \frac{\Delta_{max}}{2}$$

$$T_{e2} = t_{max} + \frac{\Delta_{max}}{2}$$

Information from multiple electrograms can, optionally, be compared by performing the above analysis on, for example, all possible pairs from groups of three electrograms, with their positions, after they have been triangulated.

The node positions 102a, 102b, 102c on the catheter are then transformed onto a 2 dimensional surface and a grid defined, with a spacing that is substantially smaller than the inter-electrode distance. At each point g on the grid, the nearest edge 104 is determined and the relative distances from the two nodes at the ends of that edge are calculated. The activation timing $T_g$ at each grid point g is then calculated as:

$$T_g = t_{max} - \frac{\Delta_{max}}{2} + \alpha \cdot \Delta_{max}$$

where α has a value of 0 if the grid location g is next to node 1 and has a value of 1 if the location is next to node 2. Each grid value is assigned to 1 at times where there exists $t-T_g<100$ ms.

This produces a set of activation times, one of each grid point g. However because of the method of calculation, the times will not be representative of a smoothly propagating wave front. Standard image smoothing algorithms are then used to create a visual display of smooth wavefront propagation. This may be performed, for example, by applying a box filter and then thresholding. Using the smooth wavefront data, a Sobel edge detector, or other suitable edge detector, is used to identify the wavefront direction at each grid point.

From the smoothed timing information describing wavefront propagation times at each grid point, direction data at each grid point is calculated.

Let the direction of a wavefront passing grid point, g, at time, t, be $d(g,t)=x(g,t)\cdot i+y(g,t)\cdot j$, where $x(g,t)$ and $y(g,t)$ are the magnitudes in two orthogonal directions (i and j) and $\sqrt{x(g,t)^2+y(g,t)^2}=1$. That direction is determined using triangulation from any group of three grid points. For example it may be calculated for each grid point using a triangular group of that grid point and two adjacent grid points g. Now the wavefront propagation across an area of interest can be described by taking the most recent activation at each point within a specified time range. The direction of the latest wave front to pass a grid point, which is a vector of unit length $d_{latest}(g,T)$=find $d(g,t)$ with $t<T$ Now, for any defined surface (usually the surface covered by the electrodes that have been analysed) can be subjected to analysis.

Wavefront direction, at a given sample time, for a particular wavefront travelling over the analysed region G(T) is calculated as the integral of latest directions for all grid points over a fixed time period, for example 200 ms, which will typically be approximately long enough so that each transition period is covered completely by one integration period, though this will of course not always be the case:

$$G(T) = \oint_s d_{latest}(g, T) ds$$

where, the wavefront direction is given by a $\tan(G_y(T)/G_x(T))$ and the wavefront 'coherence' is given by $\|G(T)\|$.

It will be appreciated that, for a given wave front, G(T) is a vector sum of directional vectors $d_{latest}$ over the transition period during which the wave front is passing through the analysed region. Therefore, assuming the wave front moves in one direction the length of the vector G(T) will increase over the transition period. If there is variation in the direction of travel of the wavefront, then the direction of the vector G(T) will also vary over that period.

Figure 6:
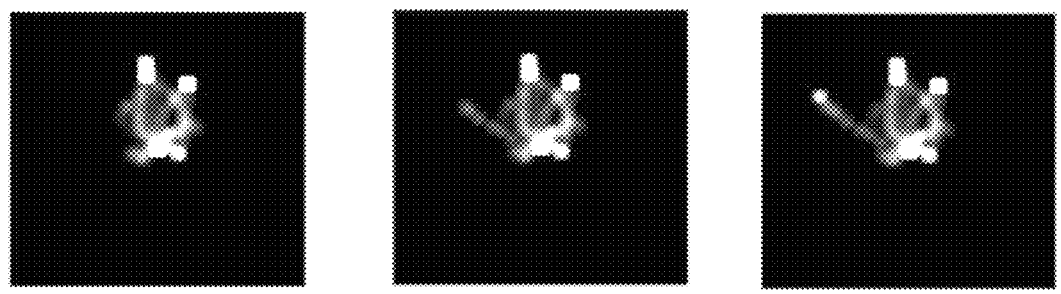
FIG. 6 shows a set of three plots generated by the system of FIG. 1 showing most recent wave front directions at three different times during passage of a further wave front.

This can be displayed as a series of dots on an x-y plot having an origin, with the dots each being located at a point which is displaced from the origin by a distance and direction corresponding to the length and direction of the integral G(T) at the time the dot is added to the display. A new dot may be displayed at regular update intervals during the transition period, and each dot displayed may be displayed for a display period, which is much longer than those regular update intervals, so that the dots are superimposed on the image during the transition period. At the end of its display period each dot may be removed from the display, or faded out. Alternatively the dots may be each be displayed continuously so that the number of dots displayed increases until the end of the measurement. This addition of a series of dots generates a line of dots for each wavefront that starts at the origin and is extended after each update interval in the direction of travel of the wavefront during that update interval. Therefore if the direction of travel is constant, the line will be straight, whereas if the direction of travel varies over the transition period, the line will be curved. This display therefore gives information about the direction and coherence of wavefronts. When a wavefront has completed its transition of the analysed region no further dots will be added to the line representing that wavefront. When a new wavefront is detected entering the analysed region, e.g. when the value of the integral G(T) changes from zero on one update interval to a non-zero value in the next update interval, a new dot is displayed at the origin and a new line of dots started for that wavefront. FIG. 6 shows the appearance of the plot as a wavefront passes the recording electrodes in a direction from bottom-right towards top-left. Panels are shown at 15 ms intervals, which is equal to the sample interval. The dots in the example shown are roughly circular, but it will be appreciated that they can be of a variety of shapes such as square or triangular.

In a modification to the process described above, the integral G(T) is calculated over much shorter time periods, for example once for each sample period. Then a new dot is displayed for each sample period, the location of the dot being determined not relative to the origin, but relative to the location of the previous dot in the line, with the new dot being offset from the previous dot in the direction of the wavefront direction just in the latest sample period.

Figure 7:
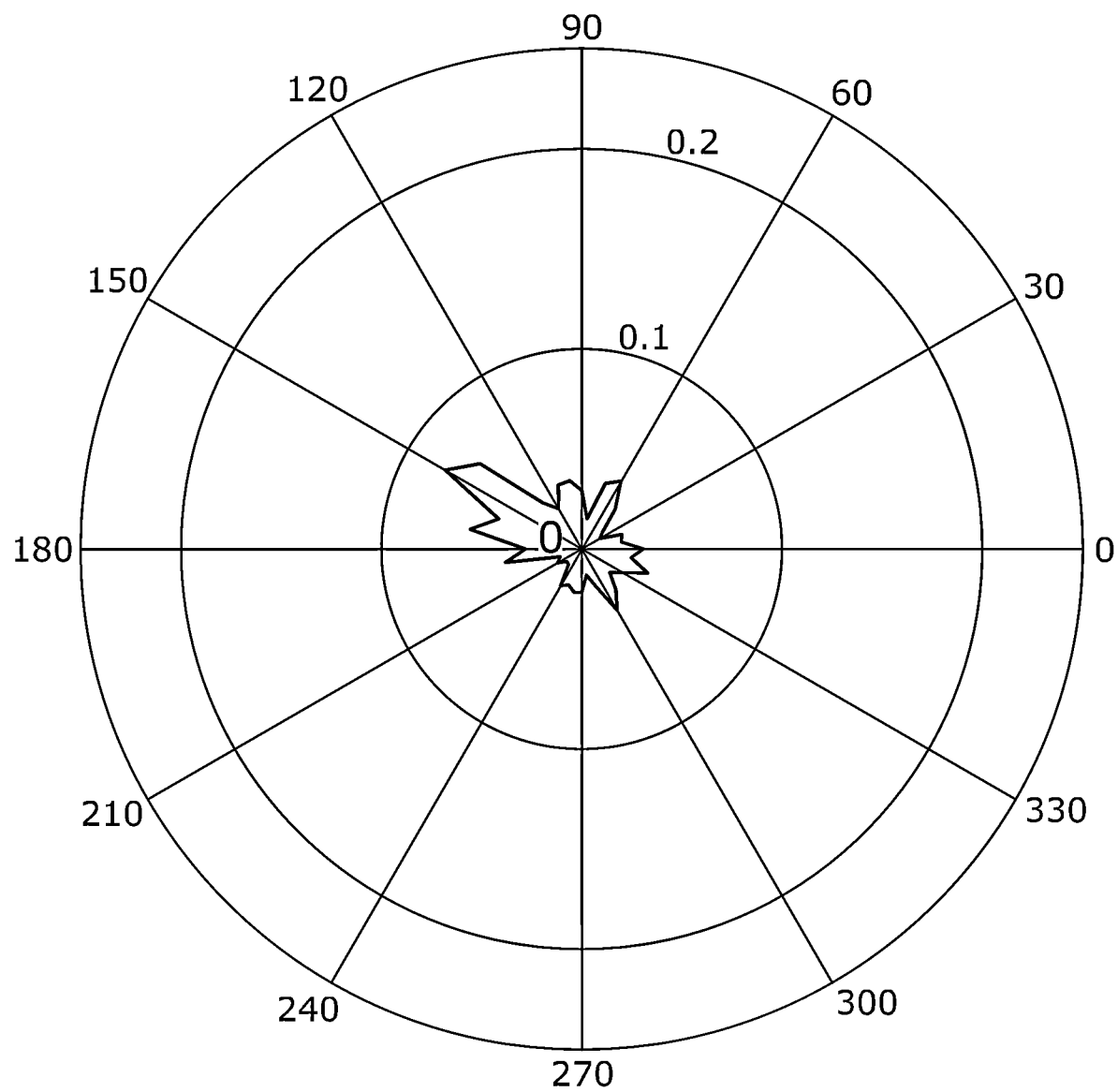
FIG. 7 shows a polar histogram plot of wave front directions generated by the system of FIG. 1.

Referring to FIG. 7, the information on wavefront direction can also be amalgamated into a polar histogram plot, weighted according to the number and coherence of wavefronts in each direction. In order to do this the wavefront direction is calculated at regular intervals, for example using the integral G(T) as described above either once for each sample interval, or once every two or three sample intervals. This generates a set of sample wavefront directions which can be displayed on a polar histogram as shown in FIG. 7.

The vector quantities $d_{latest}$ at each of the grid points any one time define a vector field over the detected region and can therefore be analysed to determine the vector operators curl and divergence at points within that region. The curl can be defined as:

$C(g,T)=\text{curl}(d_{latest}(g,T))$ and the divergence can be defined as $D(g,T)=\text{div}(d_{latest}(g,T))$ These are calculated for each point g on the grid from the values of $d_{latest}$. The divergence and curl are calculated at each grid point g using the vector that represents the last wavefront direction at neighbouring grid points. (Thus the speed of the wavefront is not used.) The divergence and curl are calculated using standard algorithms. In a neighbourhood, let x and y be the distance along two orthogonal vectors (i and j) on the heart surface. At each grid point g, the wavefront direction, d, can de represented as the sum of two vectors:

$$d(x,y)=ui+vj$$

Where d(x,y) has been normalised to have a magnitude of 1.

Divergence and Curl are then calculated for each grid point g as:

$$\text{divergence} = \frac{\partial u}{\partial x} + \frac{\partial v}{\partial y}$$

$$\text{curl} = \frac{\partial v}{\partial x} - \frac{\partial u}{\partial y}$$

The wavefront divergence and curvature may be used to highlight locations where there is rotor (or rotational) activity and also where there are focal sources or wavefront collision. Specifically maxima, or high values, of curl are associated with rotors, and maxima or values of high divergence are associated with focal sources. Therefore these maxima or high values can be located as described below and used to indicate the location of tissue that can be ablated.

Figure 8A:
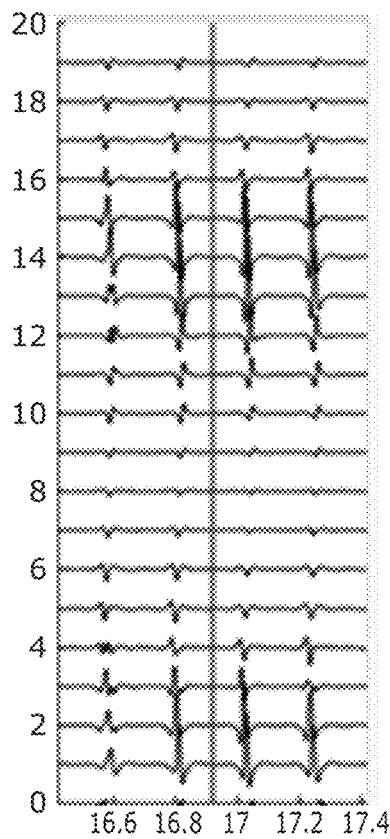
FIGS. 8A-8D show the main steps in a method according to an embodiment of the invention.
Figure 8B:
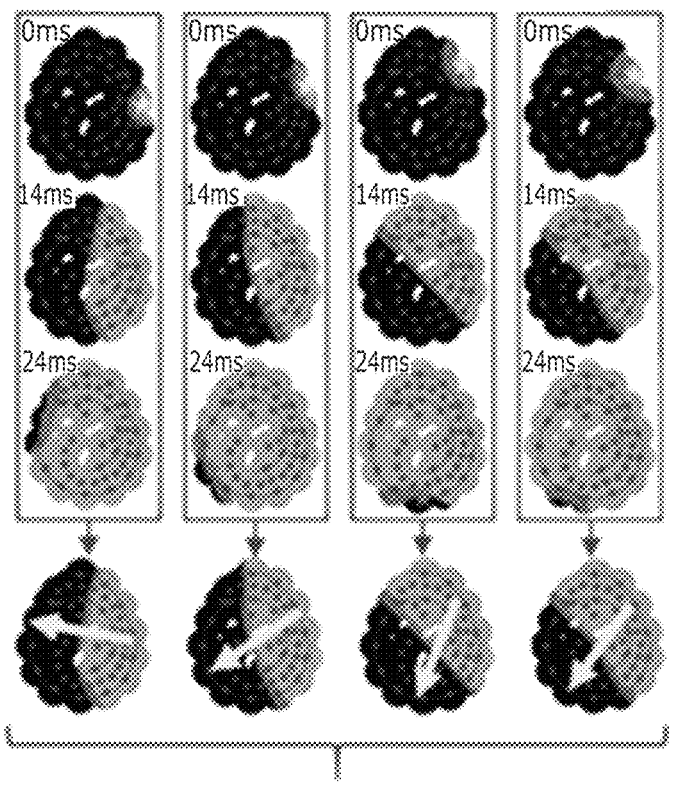
Figure 8C:
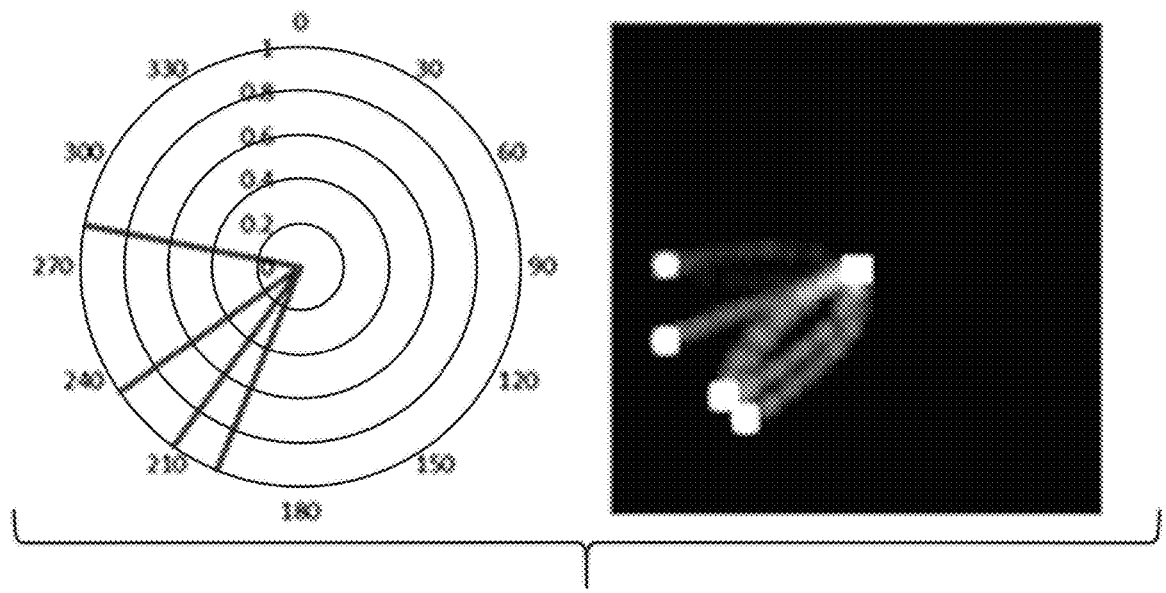
Figure 8D:
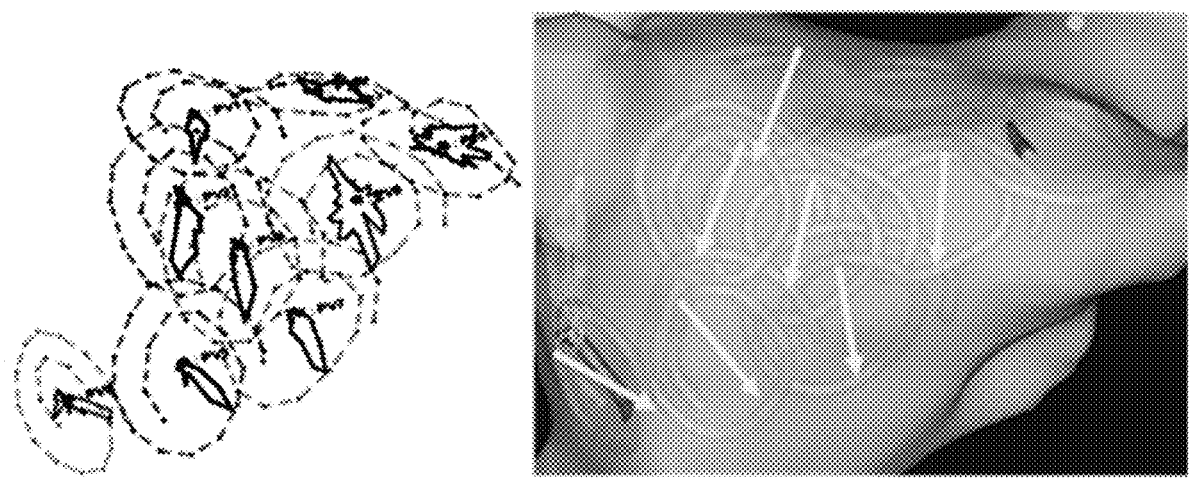

Referring to FIGS. 8A-8D, the operation of the system can be described as follows. Firstly at step A, shown in FIG. 8A, the electrogram data for each of the electrodes 102 on the probe 101 is acquired for a first position of the probe 101 and a corresponding region of the heart. Then at step B, shown in FIG. 8B, the electrogram data for that position over a sample time period is analysed as described above to determine the direction of propagation, and optionally also the coherence, of each wave front passing through that region in the total sampling time is determined. In the example shown, the probe 101 has a spiral array of electrodes 102, with the electrode positions or nodes shown in FIG. 8B. At step C, shown in FIG. 8C, data relating to the directions of wavefront propagation is displayed as an image on the display screen 110, for example as vectors on a polar plot, or a moving dot pattern as described above with reference to FIG. 6, for the region in which the probe 101 is located. The probe 101 is then moved to a second position and then subsequent positions, and in each position further data acquired, analysed and displayed. The data for each position is stored, together with probe location data indicative of the location of the probe and hence the position on the heart of the region currently being examined. At step D, shown in FIG. 8D, from this location data, the individual wave front direction images are mapped onto an image of the heart. The individual wavefront direction images may be shown as vector plots or dot images, or indeed as histogram plots or simple directional indicators as shown in FIGS. 8C and 8D.

On the image of the heart, the location of sources of fibrillation may then be determined by the user from the directional information displayed. Alternatively the processor 108 may be arranged to determine the location of sources and to control the display 110 to indicate the location of the sources on the image. For example the processor may be arranged to calculate the curl of the wavefront direction vector at positions on the heart as described above, locate a maximum of the curl, and identify the position of that maximum as the position of a rotor. The processor may then be arranged to control the display 110 to highlight, for example using arrows or colour or an outline, the position on the heat of the rotor. Alternatively the processor may be arranged to calculate the divergence of the wavefront direction vector at positions on the heart as described above, locate a maximum of the divergence, and identify the position of that maximum as the position of a focal source. The processor may then be arranged to control the display 110 to highlight, for example using arrows or colour or an outline, the position on the heat of the focal source.

Once the location of the rotor has been determined, the ablation tip 114 of the catheter, or a separate ablation catheter, is used to ablate heart tissue at the location of the rotor.

Figure 9:
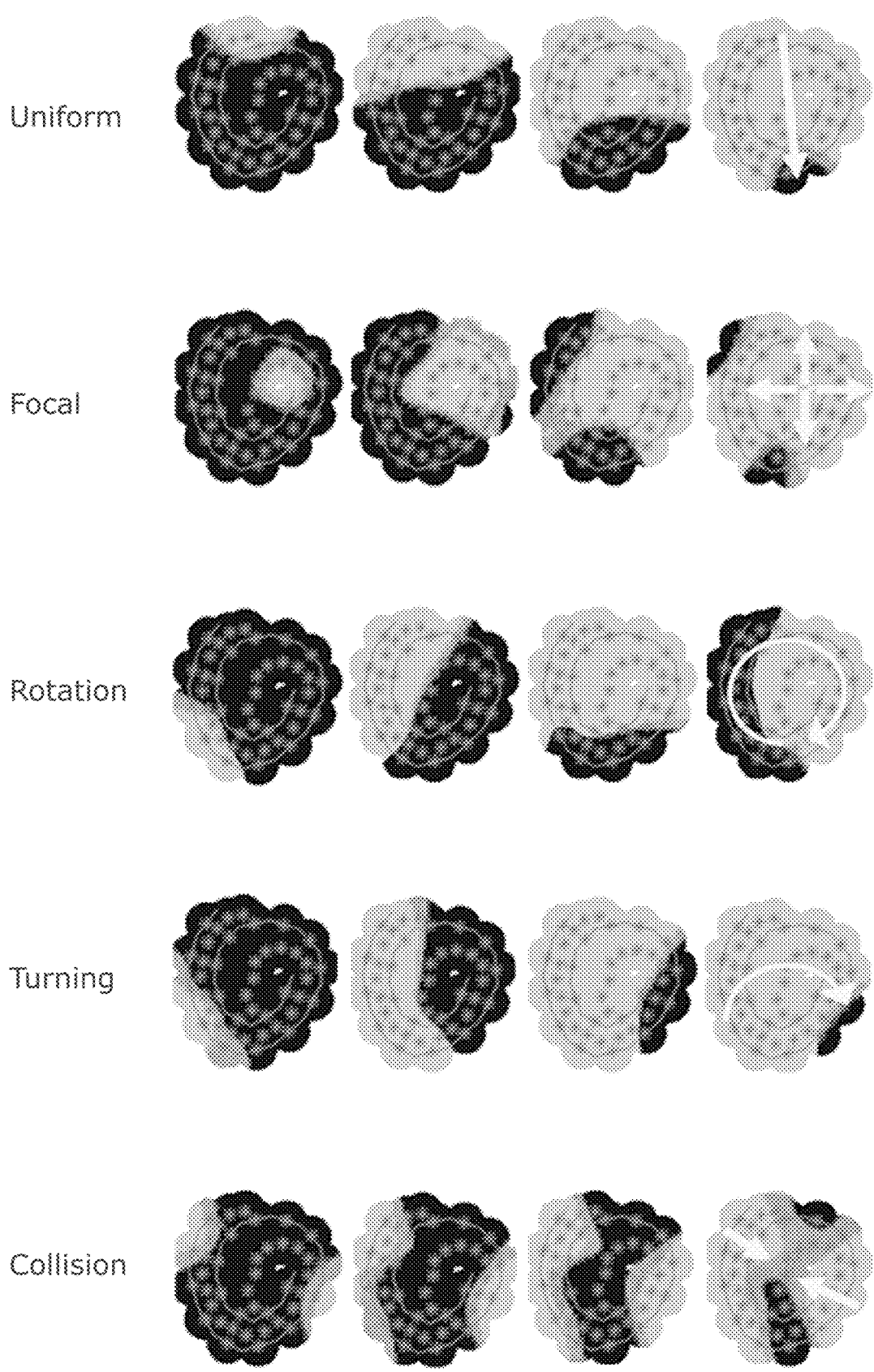
FIG. 9 shows examples of wave front patterns detected an analysed by the system of FIG. 1.

Referring to FIG. 9, the system of FIG. 1 can be arranged to differentiate between further different wave front patterns using the divergence and curvature (curl) of the wave front directions. The first set of four images in FIG. 9 shows the detection of a relatively uniform wave front passing across the region of the heart that is being contacted by the probe 101. The second set of four images shows the detection of a wave front propagating out from a focal point in the imaged region of the heart. The third set of four images shows a wave front that is rotating about a point generally at the centre of the imaged region of the heart. The fourth set of four images shows the detection of a wave front that is turning about a point outside (in this case below as seen in FIG. 9) the imaged region of the heart. Finally the last set of four images in FIG. 9 shows the detection of a pair of wave fronts colliding at the centre of the imaged region of the heart.

Figure 10:
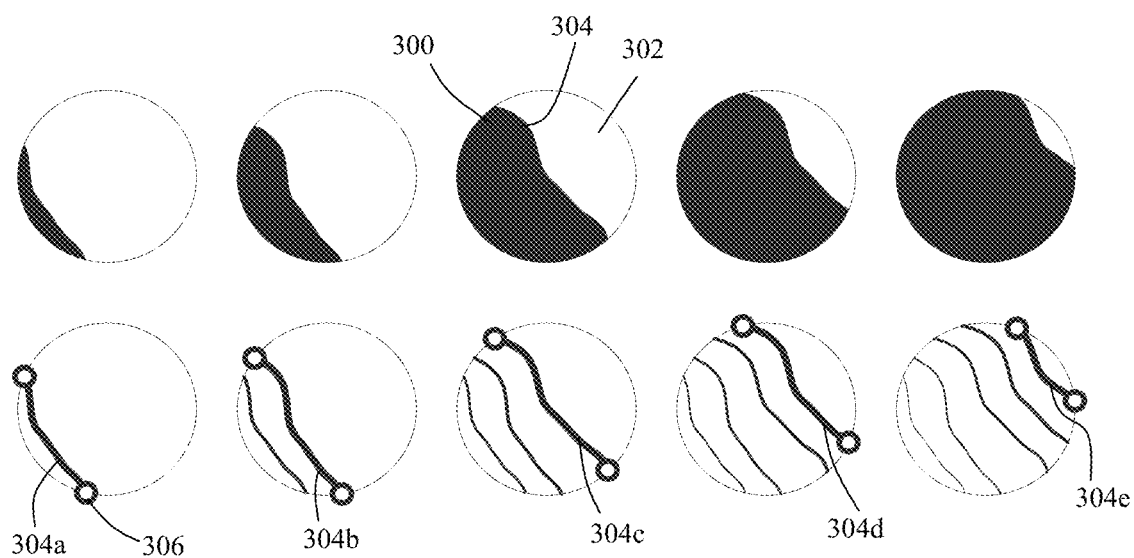
FIG. 10 shows the identification of a series of wavefront positions during transition of a wavefront across a region of the heart.

There are various ways of identifying the time of activation at each node, i.e. the position of each electrode, and identifying, monitoring, and categorizing the activation wavefronts as they pass through the monitored region. Referring to FIG. 10, in one approach the processor is arranged to identify at each of a series of update intervals those electrodes at which an activation has been detected. A map of the monitored region of the heart can then be defined which identifies an area 300 in which electrodes have experienced an activation and another area 302 in which the electrodes have not experienced an activation. The top row of FIG. 10 shows a sequence of maps for a corresponding sequence of update intervals in which the activated area 300, which is shown in black, moves or expands across the monitored region from bottom left to top right. In each map, the boundary 304 between the activated area 300 and the non-activated area 302 defines the wavefront.

The bottom row of FIG. 10 shows the current wavefront after each update interval, together with the locations of the wavefront after each previous update interval. The wavefronts may be displayed as an image which updates after each update interval and adds the latest wavefront position to those already displayed. This would result in an image that changes from the left hand image to the right hand image of the bottom row of FIG. 10 as the wavefront crosses the monitored region, moving from position 304a to 304e through the intermediate positions of 304b, 304c, 304d in between. For emphasis the latest wavefront position after each update interval may be indicted more brightly than the others as shown in FIG. 10. Each wavefront may be further faded in each subsequent image update in which it is displayed.

As described above the system may be arranged to characterize the wavefronts. In one method of doing this, the concept of child and parent wavefronts is used. A wavefront is a child wavefront of a wavefront that precedes it, for example 304e is a child of 304d, and a wavefront is a parent wavefront of a wavefront that follows it, so 304a is a parent of 304b, and 304b is a parent of 304c. The point at which a wavefront has an end, either within the image or where the wavefront meets the edge of the image (i.e. the edge of the monitored region) is defined as an endpoint 306.

Figure 11:
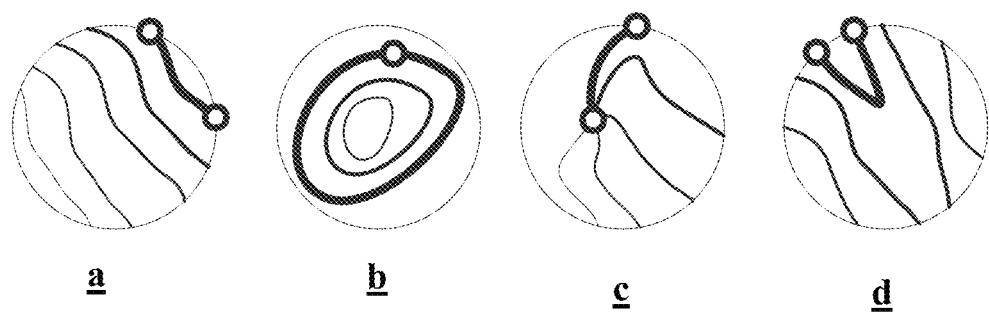
FIG. 11 shows how different types of wavefront can be identified.

These features allow various wavefront shapes, or types of activation, to be identified, as shown in FIG. 11.

Plane wavefront (a) satisfies all of:
A wavefront with both endpoints at the edge of the field of view (i.e. on the outer circle).
Either 1 parent or no parents.
Either 1 child or no children.
Focal wavefront (b) satisfies all of:
Either 1 parent wavefront which is also focal, or no parents
The endpoint of the wavefront meets the wavefront (i.e. the wavefront is a loop).
Rotating wavefront (c) satisfies all of:
One endpoint is within the field of view (i.e. one endpoint is 'floating' within the outer circle).
Collision wavefront (d) satisfies all of:
2 or more parent wavefronts.

These categorizations may be used displayed to a user in various ways, for example using different colours on a display for different categorizations of wavefront, or using labelling, depending on the purpose of the investigation being carried out.

Figure 12:
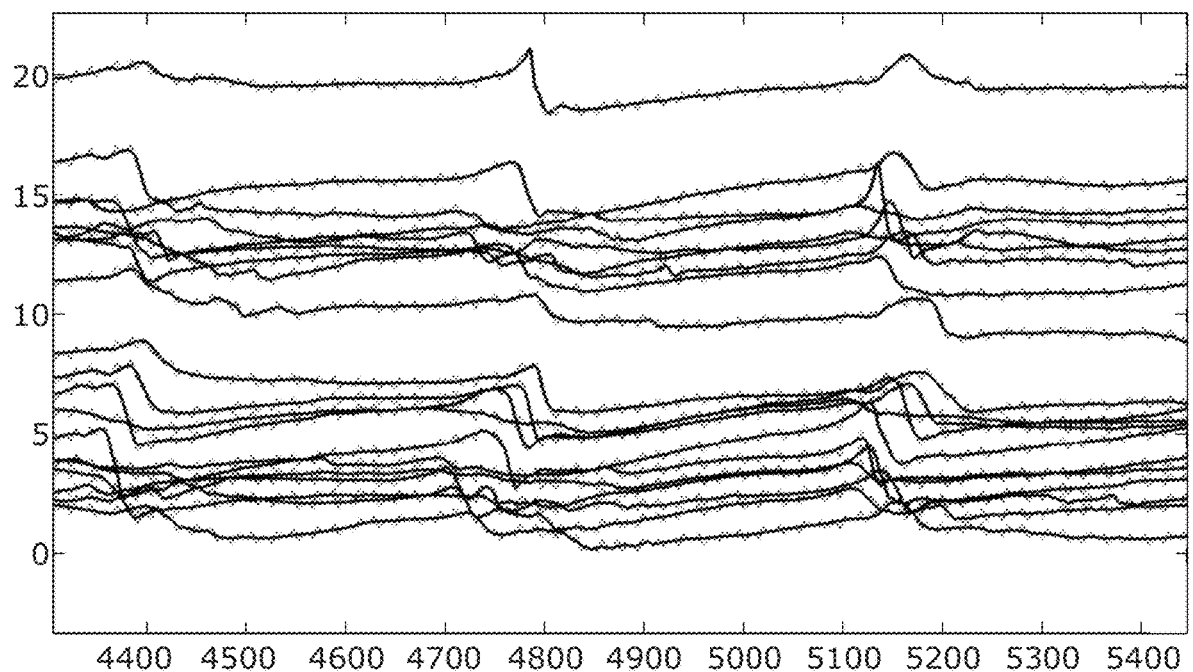
FIG. 12 is a plot of measured unipolar electrograms and corresponding filtered unipolar electrograms.

Referring to FIG. 12, the raw (un-filtered) electrogram data from the individual electrodes, plotted as voltage V as a function of time t, includes both the underlying unipolar voltages, which include sharp drops caused by the activations, and noise which is superimposed on the underlying voltages, and shown as a separate signal varying about each of the underlying voltage signals. The noise is typically of a relatively high frequency, but needs to be filtered out without removing the sharp drops in the underlying voltages. In order to do this, it can be assumed that the noise in the signals will be, in general, common to all, or several, of the individual signals. This means that features having (approximately) the same shape occur at (approximately) the same time in some or all of the individual signals. In contrast, the sharp variations in voltage which are used to identify the activations occur at different times in the different signals and are therefore not common, at least in timing, to all of the signals. A filtering method is therefore used which takes into account not just the individual unipolar electrograms, but measurements of the difference between voltages at a pair of electrodes. This enables the system to distinguish between noise features and activation features, based on the similarities and differences between the individual unipolar electrograms. This enables the system to filter the individual electrogram signals so as to filter out the noise features and retain the activation features. While a difference between two voltages is a simple and effective measure, it will be appreciated that other linear combinations of two or more signals, for example including different weightings applied to the different signals, could also be used.

Firstly to understand the advantages of including the voltage differences in the analysis, it is helpful to consider the situation in which the time varying aspect of the voltages is ignored. Consider the situation where there are two electrodes (A and B). The voltage at each electrode is measured, and also the voltage difference between the two electrodes is measured directly. At a particular time the following data is recorded: $V_a=0.8$, $V_b=1.2$, $V_{b-a}=0.2$. It is known that the direct measurement $V_{b-a}$ is subject to much less noise than $V_a$ and $V_b$. The best estimate of the underlying state is that $V_{aEst}=0.9$, $V_{bEst}=1.1$. This estimate preserves the very accurate measurement of the difference between the voltages (0.2) and has assumed an equal magnitude of error in $V_a$ and $V_b$.

Then considering a time-varying system with just two electrodes, measurements can be made of the potential difference between the electrodes and the skin—two unipolar voltage signals, u1 and u2. Measurement can also be made of the bipolar voltage, $b_1=u_1-u_2$. The aim is to estimate unipolar signals utilising the information from all the measurements that have been made: in clinical practice, the bipolar measurements (i.e. differences between unipolar electrograms) have much less noise because of common mode noise rejection.

The aim is to estimate the underlying state, i.e. the actual voltages at each of the electrodes:

$$X=(u_1,u_2) \tag{1}$$

The noisy measurements Y are used, which are made up of the noisy measurements of $u_1$, $u_2$ and $b_1$:

$$\tilde{Y}=(\tilde{u}_1,\tilde{u}_2,\tilde{b}_1)=XH+\text{noise} \tag{2}$$

Where H is an observer matrix:

$$H = \begin{pmatrix} 1 & 0 & 1 \\ 0 & 1 & -1 \end{pmatrix} \tag{3}$$

It will be noted that the observer matrix defines the linear combination, here a simple difference between the two electrograms, which is used in addition to the individual unipolar electrograms. For the more general case with more than two electrodes, the observer matrix defines for which pairs of electrodes the voltage difference is measured and used.

In a corresponding manner, an observer matrix can be used in a system with multiple (more than two) electrodes and time varying signals to estimate the unipolar voltages. For example a method based on a Savitsky Golay filter may be used. This estimates each of the unipolar signals to be modelled by a polynomial having a number of terms with respective weights, and estimates the weights using a least squares fit to the measured data, which includes the unipolar electrograms and measurements of the difference between pairs of the electrodes.

Consider a timeframe z that consists of M samples at interval dt around $t_0$.

$$z = \frac{t-t_0}{dt} = \left( \frac{-(M-1)}{2}, \frac{-(M-3)}{2}, \ldots 0, \ldots, \frac{(M-3)}{2}, \frac{(M-1)}{2} \right) \tag{4}$$

For each individual electrogram recording assume it is well modelled by a local polynomial with order n:

$$y_k(z)=\beta_0+\beta_1 z+\beta_2 z^2+\beta_3 z^3+\beta_4 z^4+\ldots+\beta_n z^n \tag{5}$$

This can be written as:

$$y_k=V\beta_k \tag{6}$$

Where V is a Vandermonde matrix:

$$V = t + dt \times \begin{pmatrix} 1 & \frac{-(M-1)}{2} & \left(\frac{(M-1)}{2}\right)^2 & \cdots & \left(\frac{-(M-1)}{2}\right)^n \\ 1 & \frac{-(M-3)}{2} & \left(\frac{(M-3)}{2}\right)^2 & \cdots & \left(\frac{-(M-3)}{2}\right)^n \\ \vdots & \vdots & \vdots & & \vdots \\ 1 & 0 & 0 & \cdots & 0 \\ \vdots & \vdots & \vdots & & \vdots \\ 1 & \frac{(M-3)}{2} & \left(\frac{(M-3)}{2}\right)^2 & \cdots & \left(\frac{(M-3)}{2}\right)^n \\ 1 & \frac{(M-1)}{2} & \left(\frac{(M-1)}{2}\right)^2 & \cdots & \left(\frac{(M-1)}{2}\right)^n \end{pmatrix} \quad [7]$$

and $$y_k = \left(\frac{y_{-(M-1)}}{2}, \frac{y_{-(M-3)}}{2}, \ldots, \frac{y_{(M-3)}}{2}, \frac{y_{(M-1)}}{2}\right)^T, \quad [8]$$

$$\beta_k = (\beta_0, \beta_1, \beta_2, \beta_3, \beta_4 \ldots \beta_n)^T$$

Now, if all of the measurements are considered they can be represented as:

$$Y = VB, \; Y = (y_1, y_2, y_3, \ldots, y_K), \; B = (\beta_1, \beta_2 \beta_3, \ldots, \beta_K) \quad [9]$$

The measurements $y_k$ (k=1, 2, ..., K) are related to the underlying states $x_j$ (j=1, 2 ... J) via the observer matrix H:

$$Y = XH, \; X = (x_1, x_2, \ldots, x_j), \; H = J \times K \text{ matrix} \quad [10]$$

Where j is the number of electrodes and k is the number of measured parameters which may be individual unipolar voltages, differences between pairs of voltages, or other linear combinations of unipolar voltages. It follows that $$x_j(z) = \alpha_0 + \alpha_1 z + \alpha_2 z^2 + \alpha_3 z^3 + \alpha_4 z^4 + \ldots + \alpha_n z^n \quad [11]$$

And $$X = VA, \; X(x_1, x_2, \ldots, x_j), \; A = (\alpha_1, \alpha_2, \alpha_3, \ldots, \alpha_j) \quad [12]$$

With $$B = AH \quad [13]$$

Then the aim is to find the J×(N+1) polynomial coefficients of A such that R, the weighted least squares residual in the estimated signals ŷ is minimised:

$$R = \sum_{k=1}^{K} R_k, \; R_k = \sum_{z=\frac{-(M-1)}{2}}^{\frac{(M-1)}{2}} w_{k,z}(\hat{y}_{k,z} - \tilde{y}_{k,z})^2 \quad [14]$$

This can be re-written in matrix form with $W_k$ being a matrix of weights $w_{k,z}$ on its diagonal:

$$R_k = (\hat{y}_k - V\beta_k)^T W_k (\hat{y}_k - V\beta_k) \quad [15]$$

To minimize R, we need $$\frac{dR}{d\alpha_j}$$

to be zero for all j. First differentiate with respect to $\beta_k$:

$$\frac{dR}{d\beta_k} = \sum_{k=1}^{K} -2V^T W_k y_k + 2V^T W_k V^T \beta_k \quad [16]$$

Then using the chain rule $$\frac{dR}{d\alpha_j} = \frac{dR}{d\beta_k} \frac{d\beta_k}{d\alpha_j} = \sum_{k=1}^{K} (-2V^T W_k y_k + 2V^T W_k V^T \beta_k) h_{jk} \quad [17]$$

Where $h_{jk}$ is the element of H form row j and column k.
Substituting $\beta_k = AH_k$, $H_k = (h_{1k}, h_{2k}, h_{3k}, \ldots, h_{jk})^T$ and setting $$\frac{dR}{d\alpha_j} = 0,$$

we obtain $$\sum_{k=1}^{K} h_{jk} V^T W_k y_k = \sum_{k=1}^{K} (V^T W_k V^T A H_k) h_{jk} \text{ for all } j \quad [18]$$

In order to solve equation [18], rearrange A and Y as vectors:

$$\vec{Y} = \begin{pmatrix} y_1 \\ y_2 \\ y_3 \\ \vdots \\ y_K \end{pmatrix} (K \times M \text{ column vector}), \quad [19]$$

$$\vec{A} = \begin{pmatrix} \alpha_1 \\ \alpha_2 \\ \alpha_3 \\ \vdots \\ \alpha_J \end{pmatrix} (J \times [n+1] \text{column vector})$$

[18] can then be re-written as $$\begin{pmatrix} h_{11} V^T W_1 & h_{12} V^T W_2 & \cdots & h_{1K} V^T W_K \\ h_{21} V^T W_1 & h_{22} V^T W_2 & \cdots & h_{2K} V^T W_K \\ \vdots & \vdots & \ddots & \vdots \\ h_{J1} V^T W_1 & h_{J2} V^T W_2 & \cdots & h_{JK} V^T W_K \end{pmatrix} \vec{Y} = \quad [20]$$

$$\begin{pmatrix} \sum_{k=1}^{K} h_{1k}(h_{1k} V^T W_k V, h_{2k} V^T W_k V, \ldots, h_{Jk} V^T W_k V) \\ \sum_{k=1}^{K} h_{2k}(h_{1k} V^T W_k V, h_{2k} V^T W_k V, \ldots, h_{Jk} V^T W_k V) \\ \vdots \\ \sum_{k=1}^{K} h_{Jk}(h_{1k} V^T W_k V, h_{2k} V^T W_k V, \ldots, h_{Jk} V^T W_k V) \end{pmatrix} \vec{A}$$

Finally an expression can be obtained for $\vec{A}$ in terms of $\vec{Y}$ $$\vec{A} = \Phi \vec{Y} \quad [21]$$

Where Φ is a matrix with [n+1]×J rows and [n+1]×K columns $$\Phi = \begin{pmatrix} \sum_{k=1}^{K} h_{1k}(h_{1k}V^T W_k V, h_{2k}V^T W_k V, \ldots, h_{Jk}V^T W_k V) \\ \sum_{k=1}^{K} h_{2k}(h_{1k}V^T W_k V, h_{2k}V^T W_k V, \ldots, h_{Jk}V^T W_k V) \\ \vdots \\ \sum_{k=1}^{K} h_{Jk}(h_{1k}V^T W_k V, h_{2k}V^T W_k V, \ldots, h_{Jk}V^T W_k V) \end{pmatrix}^{-1} \quad [22]$$

$$\begin{pmatrix} h_{11}V^T W_1 & h_{12}V^T W_2 & \ldots & h_{1K}V^T W_K \\ h_{21}V^T W_1 & h_{22}V^T W_2 & \ldots & h_{2K}V^T W_K \\ \vdots & \vdots & \ddots & \vdots \\ h_{J1}V^T W_1 & h_{J2}V^T W_2 & \ldots & h_{JK}V^T W_K \end{pmatrix}$$

The matrix Φ is dependent only upon the observation matrix H and the weights $W_k$, that have been chosen for each signal measurement. For continuous signals the estimate of the underlying states, $\hat{X}$ can be calculated efficiently as a convolution operation with Y.

The weights $W_k$ can also be considered as a series of windows for each signal measurement. Selecting a long timeframe (M—see equation [4]), a low polynomial order (n—see equation [5]) and a uniform window $W_k$= [1 1 1 . . . 1] will result in a low-pass filter being applied to signal k. Conversely a window with weights that are high only in the central regions will preserve higher frequencies. For example, using $W_k$=[0 0 1 1 1 0 0] results in a window length of 3 being applied to signal k and allows window lengths of up to 7 to be used for other signals.

As mentioned above, the observer matrix H can be selected to include useful linear combinations of the unipolar voltages. In one example, as well as the individual unipolar voltages, the difference between the voltage at each electrode and the adjacent electrode is included, i.e. the unipoles and 'sequential bipoles'. For four electrodes 1 to 4, this would be V(1) V(2) V(3) V(4) V(2-1) V(3-2) V(4-3). In some cases it is advantageous to measure more of the bipole 'options' because the noise in any bipole signal may be dependent on how far apart the two electrodes are. If the electrode positions are known, then the weighting of the errors used in the minimisation can be arranged to relate to the expected noise level.

The weights $W_k$, that are chosen for each signal measurement can be used to select the relative weight of the different signal measurements. In this method they can also provide filtering in that they can be used to select the relative weight of different frequency components for each signal measurement as described above. For example in the bipolar electrograms there is a reduction of noise but also a loss of the high frequency signal components. However by incorporating bipolar electrograms in the model it is possible to recover the high frequency information. This is done by using weights (e.g. $W_k$ in equation 22) that are different for the bipolar signals and preserve the high frequency information. The measurement model enables the combination of this high frequency information with the lower frequency information that is present in the filtered unipolar electrograms.

Figure 13:
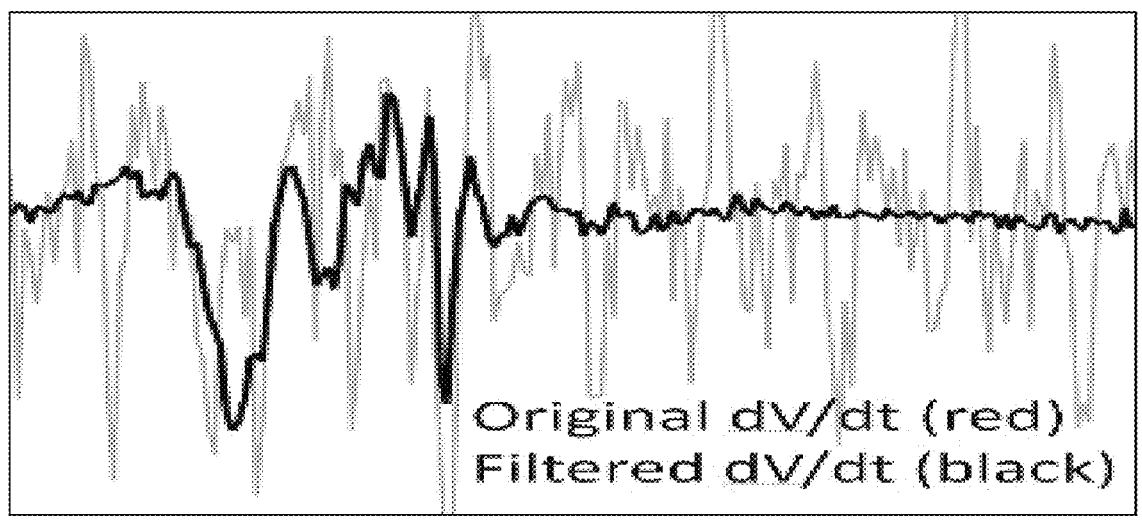
FIG. 13 is a plot of the time derivative of a unipolar electrogram of FIG. 12 and the time derivative of the corresponding filtered unipolar electrogram.

FIG. 13 shows the results of a filter as described above, in which the gradient (time differential) of one of the unipolar electrograms is plotted, as a function of time, for the raw unfiltered and the filtered electrograms. As can be seen the filtered data shows much less noise and the steep negative gradients which are indicative of activation events are much more clearly identified.

Figure 14:
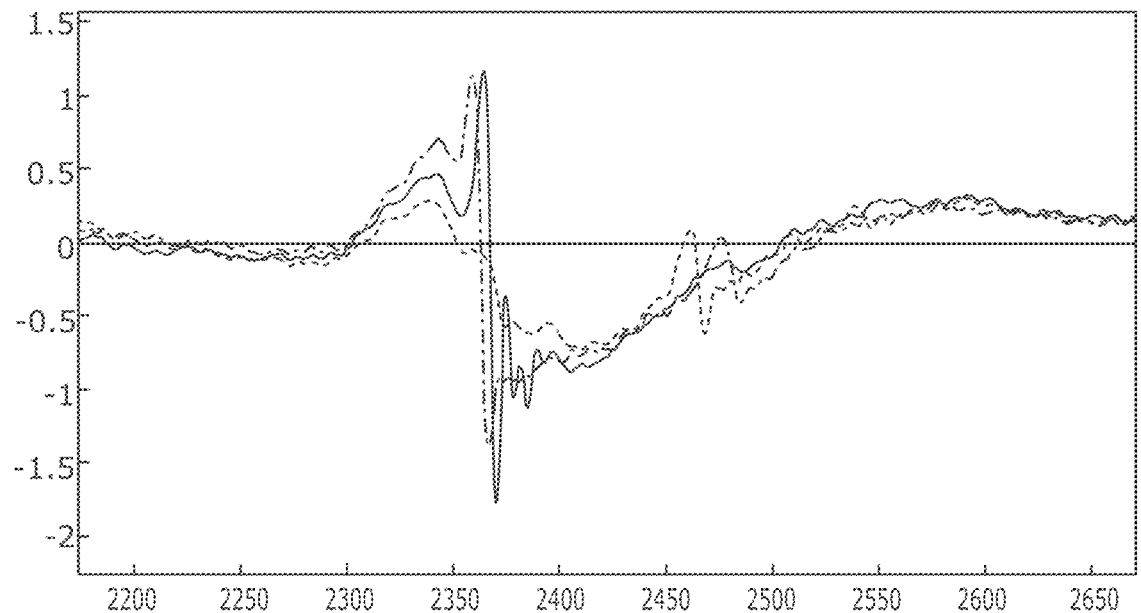
FIG. 14 is plot of three filtered unipolar electrograms similar to those of FIG. 12, showing only a section centred on an activation event.
Figure 15:
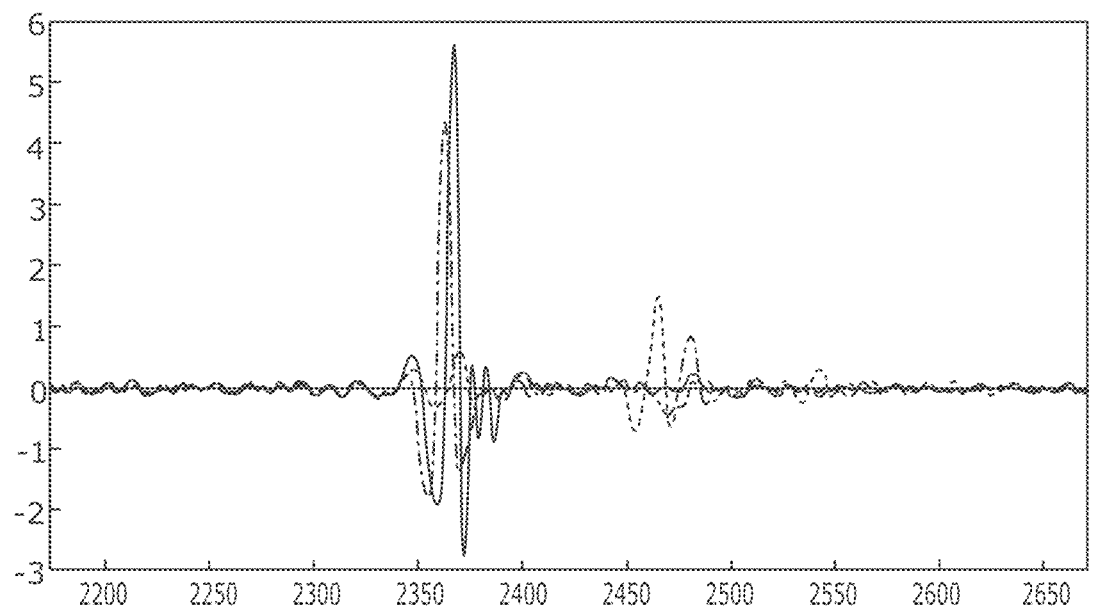
FIG. 15 shows convolutions of the plots of FIG. 12 with a plot of 1/t.

Once the electrogram data has been filtered, the time at which an activation event occurs at each electrode, i.e. the time at which a wavefront passes that electrode, needs to be identified. FIG. 14 shows examples of electrograms of three different activation events, shifted so that they occur at about the same time and are centred on V=0. It is noted that the shape of the electrogram plot around the time of an activation event is similar to a plot of 1/t as a function of t. Therefore in order to locate the activation events, a convolution with 1/t is applied to the filtered electrograms of FIG. 12 (for example a Hilbert filter) which results, after filtering out low frequency noise using a digital linear phase filter, in the plots shown in FIG. 15 with peaks clearly identifying the location in time of the activation events.

The invention claimed is:

1. An apparatus for monitoring activation in a heart, the apparatus comprising a probe, a plurality of electrodes supported on the probe and extending over a detection area of the probe, the detection area being arranged to contact a detection region of the heart, wherein each of the electrodes is arranged to detect electrical potential at a respective position in the heart during movement of a series of activation wavefronts across the detection region, a display screen, and a processor configured to:
    process and analyse the detected electrical potentials to identify a plurality of wavefronts passing the detection region;
    for each of the plurality of wavefronts, identify a transition period during which the wavefront crosses the detection region and define a series of update intervals occurring during the transition period;
    for each of the update intervals to determine a propagation direction; and to control the display screen to generate a display indicative of the direction.

2. The apparatus according to claim 1 wherein processor is configured to process the detected electrical potentials by filtering them to remove noise.

3. The apparatus according to claim 2 wherein the processor is configured to record values of the electrical potential at each of the electrodes as a respective unipolar electrogram, and to perform filtering on the unipolar electrograms to filter out noise from the unipolar electrograms.

4. The apparatus according to claim 3 wherein, in filtering the unipolar electrograms, the processor is configured to filter out from the unipolar electrograms noise features which are common to a plurality of the unipolar electrograms.

5. The apparatus according to claim 3 wherein, in filtering the unipolar electrograms, the processor is configured to retain in the unipolar electrograms, features which are unique to each of the unipolar electrograms.

6. The apparatus according to claim 3 wherein, in filtering the unipolar electrograms, the processor is configured to define a multi-electrode model which defines the unipolar signal at each of the electrodes, and to identify a best fit of the model to the unipolar electrograms.

7. The apparatus according to claim 6 wherein the model defines the difference between the two unipolar signals in each of a plurality of pairs of the unipolar signals and the processor is configured to determine from the unipolar electrograms measured values of said differences, and to use the modelled and measured differences in identifying the best fit.

8. The apparatus according to claim 1 wherein the processor is configured to identify at least one of the wavefronts as belonging to one of a plurality of classifications depending on at least one of its shape, its position, and its direction of travel.

9. An apparatus for monitoring activation in a heart, the apparatus comprising a probe, a plurality of electrodes supported on the probe and extending over a detection area of the probe, the detection area being arranged to contact a detection region of the heart, wherein each of the electrodes is arranged to detect an electrical potential at a respective position in the heart during movement of a series of activation wavefronts across the detection region, a display screen, and a processor configured to:

record the detected electrical potential at each of the electrodes as a unipolar electrogram;

forming an electrogram combination which is a linear combination of at least two of the unipolar electrograms and which is affected more by a change in just one of the two electrical potentials than it is by the same change in both of the two electrical potentials;

filter out noise in the unipolar electrograms based on the degree to which the noise is more present in the individual unipolar electrograms than it is in the electrogram combination.

10. The apparatus according to claim 9 wherein the processor is configured to filter out the noise by:

defining a model of the electrical potentials at all of the electrodes;

defining a voltage combination which is a linear combination of at least two of the electrical potentials in the model;

finding a best fit of the model and the voltage combination to the unipolar electrograms and the electrogram combination.

11. The apparatus according to claim 10 wherein the processor is configured to define a measurement matrix recording the unipolar electrograms and the electrogram combination, and an observer matrix which relates the measurement matrix to the model.

12. The apparatus according to claim 10 wherein the voltage combination is a difference between two of the electrical potentials.

13. The apparatus according to claim 11 wherein the observer matrix defines a plurality of voltage combinations each of which is the linear combination of a different pair of the electrical potentials.

14. The apparatus according to claim 11 wherein the processor is configured to define a weighting for each of the unipolar electrograms and the electrogram combination.

15. The apparatus according to claim 14 wherein the weightings are frequency dependent.

16. The apparatus according to claim 9 wherein the processor is configured to analyse each of the unipolar electrograms to identify any tissue activation features that they contain which are indicative of one of the activation wavefronts.

17. The apparatus according to claim 16 wherein the processor is configured to analyse each of the unipolar electrograms using a convolution with an inverse function of time.

* * * * *